United States Patent [19]

Cheiky-Zelina

[11] Patent Number: 5,504,573
[45] Date of Patent: Apr. 2, 1996

[54] APPARATUS AND METHOD FOR ANALYZING PARTICLES DEPOSITED ON A SUBSTRATE USING SUBSTANTIALLY CONTINUOUS PROFILE DATA

[75] Inventor: Margaret A. Cheiky-Zelina, Cleveland, Ohio

[73] Assignee: Man-Gill Chemical Company, Cleveland, Ohio

[21] Appl. No.: 135,683

[22] Filed: Oct. 13, 1993

[51] Int. Cl.$^6$ .......................... G01N 33/28; G01N 21/00; G01T 1/167

[52] U.S. Cl. .......................... 356/70; 356/440; 356/442; 356/436; 250/301

[58] Field of Search .................................. 356/432, 433, 356/434, 436, 70, 440, 441, 442; 250/301; 73/53.05, 53.07

[56] References Cited

U.S. PATENT DOCUMENTS

| | | | |
|---|---|---|---|
| 3,892,485 | 7/1975 | Merritt et al. | 356/70 |
| 3,981,584 | 9/1976 | Guymer | 356/70 |
| 4,047,814 | 9/1977 | Westcott | 356/70 |
| 4,187,170 | 2/1980 | Westcott et al. | 209/1 |
| 4,492,461 | 1/1985 | Jones et al. | 356/70 |
| 4,986,664 | 1/1991 | Lovoi | 356/376 |
| 5,218,211 | 6/1993 | Cresswell et al. | 356/338 |
| 5,309,213 | 5/1994 | Desjardins et al. | 356/70 |

FOREIGN PATENT DOCUMENTS

| | | |
|---|---|---|
| 0080699 | 6/1983 | European Pat. Off. . |
| 2151419 | 4/1973 | France . |
| 56-166444 | 12/1981 | Japan . |
| 50-213227 | 12/1983 | Japan . |
| 1415311 | 11/1975 | United Kingdom . |
| 1415312 | 11/1975 | United Kingdom . |
| 2099140 | 12/1982 | United Kingdom . |

OTHER PUBLICATIONS

Laghari et al, "Computer Vision System for the Recognition of Wear Particles", ICARCV '92, Singapore, Sep. 16–18, 1992, Nayang Technol. university, CV–13.6, vol. 1, pp. 1–5.

Liu et al, "Research on an On–Line Ferrograph", Wear, vol. 153, No. 2, Apr. 1, 1992, pp. 324–330.

Roylance et al, "Computer–Aided Vision Engineering (CAVE)—Quantificatio of Wear Particle Morphology", Lubric Ation Engineering, vol. 50, No. 2, Feb. 1994, pp. 111–116.

Roylance et al, "Wear Studies Through Particle Size Distribution II: Multiple Field Analysis in Ferrography", Wear, vol. 90, No. 1, Sep. 15, 1983, pp. 137–147.

*Primary Examiner*—Frank Gonzalez
*Assistant Examiner*—Jason D. Eisenberg
*Attorney, Agent, or Firm*—Renner, Otto, Boisselle & Sklar

[57] ABSTRACT

An apparatus for analyzing particles collected from a fluid and deposited on a substrate along a given direction, the apparatus including holding structure for supporting the substrate; a radiation source for directing radiation toward the particles on the substrate; and a radiation detector for receiving radiation incident upon the particles on the substrate and for providing an output based on the concentration of the particles, the radiation detector being cooperative with the radiation source to output substantially continuous profile data indicative of the concentration of said particles along the given direction.

24 Claims, 4 Drawing Sheets

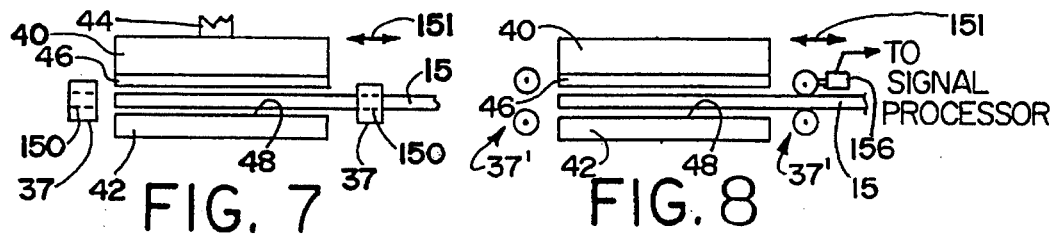
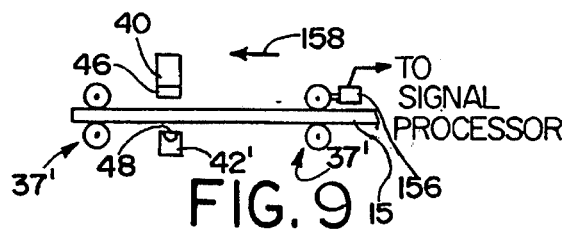
FERROGRAPHIC EXPERT SYSTEM:
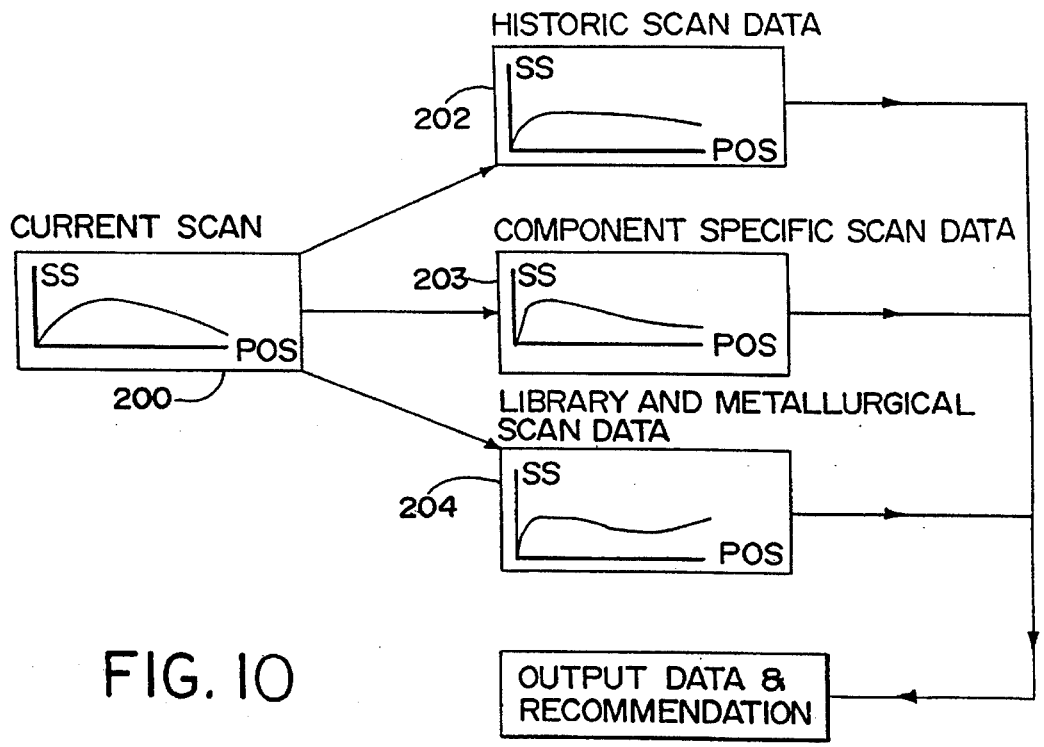
FIG. 10

APPARATUS AND METHOD FOR ANALYZING PARTICLES DEPOSITED ON A SUBSTRATE USING SUBSTANTIALLY CONTINUOUS PROFILE DATA

TECHNICAL FIELD

The present invention relates generally, as is indicated, to a system for analyzing particles deposited on a substrate. More particularly, the present invention relates to a system for evaluating the condition of a machine based on an analysis of such particles.

BACKGROUND OF THE INVENTION

Wear particle analysis is known. Wear particle analysis is a machine condition monitoring program for lubricated equipment. By examining the particles contained in the lubricant, wear related failures can be identified at an early stage. Wear particle analysis is conducted typically in two stages. The first stage involves monitoring and trending wear particles in the lubricant to detect abnormal wear. The second stage involves further analysis to identify, for example, the wear mechanisms causing particle formation, the sources of the particles, and hence the wearing components.

In order to monitor and trend wear particles in a lubricant, a sample of the particulate is typically taken from the lubricant. For example, Westcott U.S. Pat. No. 4,047,814 describes a method and apparatus for segregating particulate matter from a fluid. The particle-containing fluid such as the machine lubricant is flowed along a path over a collecting substrate in the presence of a magnetic or electric field having an intense gradient. The result is a stripe pattern of deposited material on the substrate, with particle size varying gradually from one end of the stripe pattern to the other. A collecting substrate having such a deposit is commonly referred to as a "ferrogram". The entire disclosure of U.S. Pat. No. 4,047,814 is incorporated herein by reference.

In the past, the deposit pattern formed on the substrate has been studied under a microscope by a laboratory technician. The laboratory technician visually compares the distribution and concentration of the particulate deposited on the substrate with previous samples to evaluate trending and the like. When abnormal wear is detected based on a changing distribution, concentration, etc., in the sample, the laboratory technician then studies the sample further in an attempt to diagnose the cause of the abnormal wear.

Unfortunately, there are several drawbacks associated with such prior art practices for analyzing wear particles. For example, visually studying a sample under a microscope is very time consuming for the technician and results in substantial labor costs. Moreover, the repeated study of samples under a microscope can lead to eye strain, fatigue, and other health related problems. Furthermore, the reliable detection and diagnosis of abnormal wear is highly dependent upon the knowledge and level of skill of the technician studying the sample. A relatively inexperienced technician, for example, may be more likely to misdiagnose abnormal wear based on the particulate than a technician having more experience.

The aforementioned U.S. Pat. No. 4,047,814 describes an automated apparatus for examining particle concentration/distribution on the substrate using a densitometer. However, the apparatus provides such particle concentration/distribution information only with respect to a few discrete locations along the deposit pattern on the substrate. The apparatus described in the '814 patent does not provide sufficient information to construct a substantially continuous profile of the particle concentration along the deposit pattern. As a result, information between the discrete locations is not considered when evaluating the particle concentration/distribution. This can lead to misdiagnoses and false negatives, for example.

According to another known automated apparatus, a pair of photodiodes are positioned adjacent the substrate at locations predetermined to hold particles of prescribed dimensions. For example, the first photodiode provides an output signal indicative of the concentration of particles which exceed a predetermined dimension, e.g., greater than 3.0 micrometers in diameter. The second photo diode provides an output signal indicative of the concentration of particles which are less than or equal to a predetermined dimension, e.g., less than or equal to 3.0 micrometers in diameter. While such an apparatus is capable of providing a rough indication of the particle concentration, the apparatus cannot provide a substantially continuous profile of the particle concentration along the deposit pattern.

Furthermore, the success rate of the above-discussed automated systems for identifying abnormal wear is still largely dependent on the level of skill of the technician. The technician must still be able to recognize and evaluate various trends, etc. in the resultant information. This can be particularly difficult in view of the limited information available to the technician from the automated apparatus. Thus, these systems are still likely to result in misdiagnoses, etc.

In view of the aforementioned shortcomings associated with conventional systems for analyzing wear particles deposited on a substrate, there is a strong need in the art for a method and apparatus for automatically analyzing the particle concentration and providing a substantially continuous profile of the concentration along the deposit pattern. Moreover, there is a strong need for a method and apparatus for automatically analyzing the deposit pattern and providing a diagnosis which is objective and less dependent on the particular level of skill of the technician.

SUMMARY OF THE INVENTION

The present invention relates to a system for scanning the deposit pattern on ferrogram substrate. By scanning the deposit pattern, the system obtains substantially continuous profile data indicative of the concentration of such particles along the length of the pattern. The system correlates the scanned information with past history information and/or other expert system libraries to provide an indication of the status of the machine from which the ferrogram is obtained. Moreover, the system is capable of automatically diagnosing abnormal wear and facilitating recommendation of machine maintenance.

According to one particular aspect of the present invention, an apparatus is provided for analyzing particles collected from a fluid and deposited on a substrate along a given direction. The apparatus includes holding means for supporting the substrate; radiation source means for directing radiation toward the particles on the substrate; and radiation detector means for receiving radiation incident upon the particles on the substrate and for providing an output based on the concentration of the particles, the radiation detector means being cooperative with the radiation source means to output substantially continuous profile data indicative of the concentration of said particles along the given direction.

According to another aspect of the present invention, an apparatus is provided for analyzing wear particles collected from a fluid from a machine and deposited on a substrate along a given direction. The apparatus includes holding means for supporting the substrate; radiation source means for directing radiation toward the particles on the substrate; radiation detector means for receiving radiation incident upon the particles on the substrate and for providing an output based on the concentration of the particles, the radiation detector means being cooperative with the radiation source means to output data indicative of the concentration of the particles along the given direction; and computer means functioning as an expert system including a knowledge base for analyzing the data and providing information relating to the condition of the machine.

To the accomplishment of the foregoing and related ends, the invention, then, comprises the features hereinafter fully described and particularly pointed out in the claims. The following description and the annexed drawings set forth certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the drawings:

FIG. 7 is a schematic view of a holding mechanism for facilitating the positioning of the ferrogram between the light collimator and photodiode array in accordance with one embodiment of the present invention;

FIG. 8 is a schematic view of a holding mechanism for automatically positioning the ferrogram between the light collimator and photodiode array in accordance with another embodiment of the present invention;

FIG. 9 is a schematic view of a holding mechanism for automatically positioning the ferrogram between a modified light collimator and photodiode in accordance with yet another embodiment of the present invention; and FIG. 10 is a systematic view of the library functions and expert system analyses in accordance with the present invention.

DETAILED DESCRIPTION OF THE PREFERRED EMBODIMENTS

The present invention will now be described in detail with reference to the drawings, wherein like reference labels are used to refer to like elements throughout.

Figure 1:
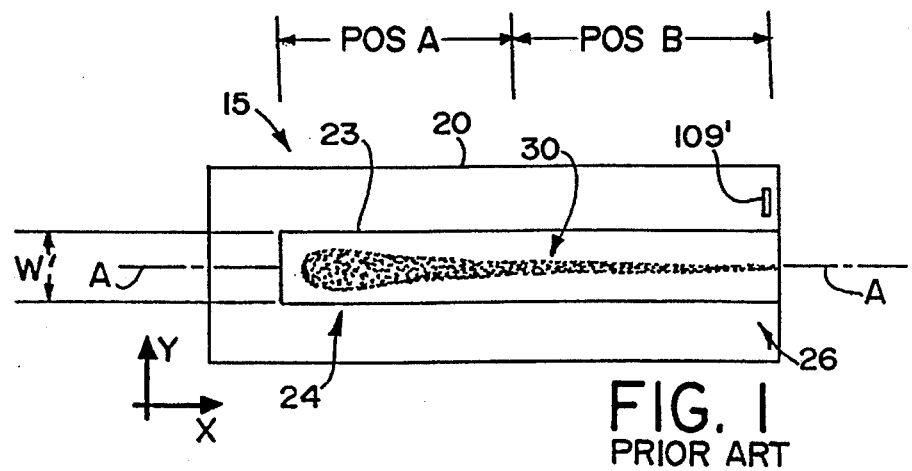
FIG. 1 is a schematic representation of a ferrogram including particulate deposited on the surface of a substrate.

Referring initially to FIG. 1, a conventional ferrogram is designated 15. As is described in detail in the above-mentioned U.S. Pat. No. 4,047,814, the ferrogram 15 includes a substrate 20 formed from a thin transparent or translucent material such as glass. The substrate 20 typically is approximately 3 mils thick, one inch wide and two inches long. During the making of the ferrogram 15, fluid from a machine is flowed in a positive x-direction along the substantial length of the substrate 20 over a flow-defining channel 23 formed on the surface of the substrate 20. The fluid may be a machine lubricant or the like which contains metal particulate due to mechanical wear, etc. The larger particles in the fluid are drawn to the substrate 20 first because of their larger volume-to-area ratio and thus are deposited at the upper or "inlet" end 24 of the substrate 20. The smaller particles, characterized by a smaller volume-to-area ratio, are deposited further down the substrate 20 toward the lower or "outlet" end 26 of the substrate. Intermediate sized particles are deposited somewhere in between. As a result, a stripe shaped deposit pattern 30 is formed on the surface of the substrate 20 representative of the particle concentration and size distribution.

Figure 2:
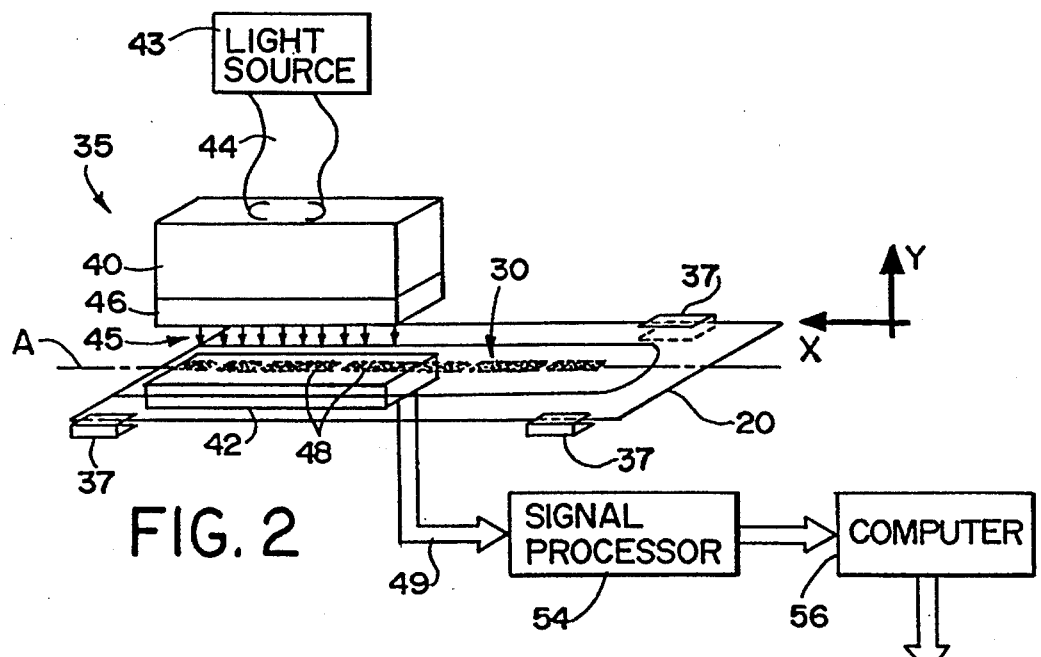
FIG. 2 is a system level diagram, in partial perspective, of a ferrogram scanning system for analyzing particulate on a ferrogram in accordance with the present invention.

Referring now to FIG. 2, a ferrogram scanning system 35 is shown in accordance with a preferred embodiment of the present invention. The ferrogram scanning system 35 includes a set of holding brackets 37 for positioning the ferrogram 15 between a light collimator 40 and a linear photodiode array 42. The light collimator 40 collimates light provided from a light source 43 via fiber optic cables 44. The light collimator 40 directs collimated light 45 which is incident on and transmitted through at least a portion of the deposit pattern 30 along the longitudinal axis A of the deposit pattern. The light collimator 40 preferably illuminates the deposit pattern 30 with light having generally uniform intensity along the longitudinal axis A. An optical filter 46 is included to filter the light 45 to reduce noise as will be appreciated.

Figure 3:
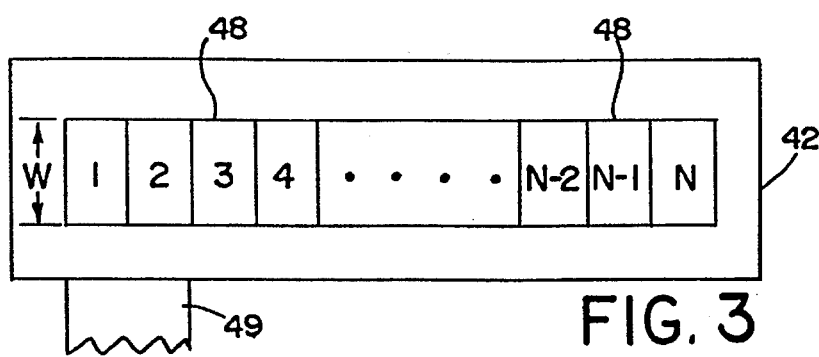
FIG. 3 is a schematic diagram of a photodiode array included in the system of FIG. 2 in accordance with the present invention.

The linear photodiode array 42 is positioned on the opposite side of the substrate 20. Referring briefly to FIG. 3, the linear photodiode array 42 includes N photodiodes 48 arranged side-by-side. In the preferred embodiment, the photodiode array 42 includes 1024 individual photodiodes 48 spaced evenly apart over approximately one inch. Thus, the linear photodiode array 42 provides an optical resolution of approximately one thousand twenty-four "pixels" per inch. The width W of each photodiode 48 is approximately equal to the width W' of the flow-defining channel 23 (FIG. 1). Each photodiode 48 detects the intensity of the light 45 which is transmitted through the deposit pattern 30 at a corresponding lineal position along the length of the deposit pattern 30 and the axis A. The output signal produced by each photodiode 48 varies in accordance with the intensity of the light received thereby as will be appreciated. The intensity of the light which is transmitted through the deposit pattern 30 at each location along the deposit pattern relates to the concentration of the particles in the deposit pattern 30 at that location. The larger the concentration of particles, the more light which is blocked by the deposit pattern 30, and thus the lower the intensity of the light which is transmitted through the substrate 20 at that location. Alternatively, the smaller the concentration of particles at a given photodiode position, the less light which is blocked by the deposit pattern 30.

Continuing to refer to FIG. 2, each photodiode 48 provides an output signal related to the intensity of the received light. The output signals from the photodiodes 48 are read out serially on line 49. The output signals from the photodiodes 48 are provided to a signal processor 54 which conditions the output signals (see FIG. 5) for further processing and/or analysis by a computer 56. The computer processes the information provided by the photodiodes 48 to produce data representing a substantially continuous profile of the concentration of the particles along the length of the deposit pattern 30. Software routines stored in the computer 56 are used to compare the profile data with historical data to evaluate trending and/or other "standard" data. As is described more fully below, the computer 56 utilizes a knowledge base stored in the computer 56 as part of an expert system whereby the system 35 evaluates the profile data and facilitates maintenance recommendations or the like. The computer 56 in the preferred embodiment is a conventional personal computer, although certainly another type of computer or processor can be utilized without departing from the scope of the invention.

The computer 56 outputs data and/or the results of the evaluations via an information output 58. The information output 58 includes, for example, a display on which the profile of the particle concentration is shown in graph form (e.g., see FIG. 4). Moreover, the information output 58 includes, for example, a display and/or printer for outputting conclusions or suggested recommendations for machine maintenance to the technician.

As with the example shown in FIG. 2, it is possible that the length of the deposit pattern 30 will exceed the length of the linear photodiode array 42. As a result, intensity readings are taken along the deposit pattern 30 in incremental steps with each step equal to the length of the N photodiode array 42. For example, the deposit pattern 30 in FIG. 1 is approximately two inches in length. The linear photodiode array 42, on the other hand, is approximately one inch in length. Accordingly, in the exemplary embodiment the photodiode array 42 and the light collimator 40 are initially positioned on opposite sides of the deposit pattern 30 at position A. A set of light intensity readings are then obtained from each of the photodiodes 48. Next, the ferrogram 15 is moved relative to the photodiode array 42 and the light collimator 40 to position B and a set of light intensity readings are again taken from the photodiodes 48. As a result, 2048 light intensity readings (1024 *2) are taken across the length of the deposit pattern 30. In an alternative embodiment, the overall length of the photodiode array 42 and the number of photodiodes therein can be increased to cover the entire length of the deposit pattern 30 at one time. In another embodiment, an automated positioning means can be utilized to move the ferrogram relative to the photodiode array 42 and light collimator 40 as is discussed below with respect to FIGS. 8 and 9.

Figure 4:
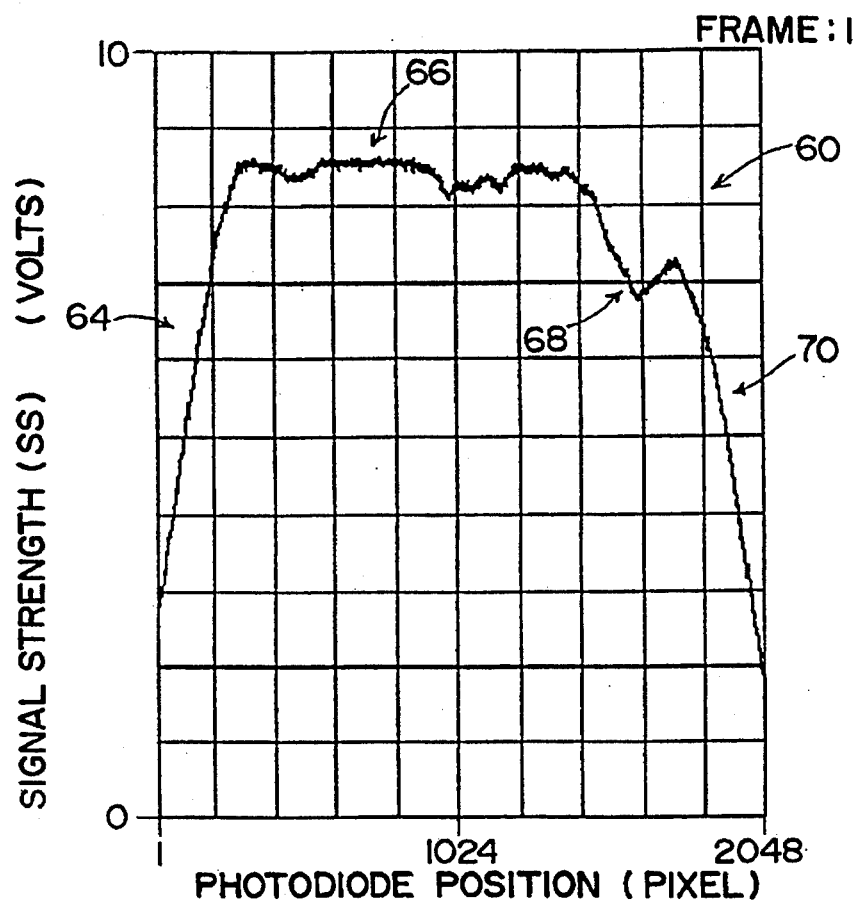
FIG. 4 is an exemplary graphical output of the system of FIG. 2 representing a substantially continuous profile of particle concentration across the length of the ferrogram deposit pattern in accordance with the present invention.

Referring now to FIG. 4, an exemplary graphical output produced by the information output 58 is shown in accordance with the present invention. The measured output of each photodiode 48 is plotted relative to the position of the photodiode along the length of the deposit pattern 30. The vertical axis represents the voltage received from the photodiode, which is inversely related to the intensity of the light received by the photodiode and directly related to the concentration of particles at the respective location. The horizontal axis represents photodiode position along the length of the deposit pattern 30. Thus, for example, at the photodiode position 1 a signal having a value equal to approximately 3.0 volts is measured representing the intensity of the light which is transmitted through the inlet end 24 (FIG. 1) of the deposit pattern 30. At the photodiode position 2048 a signal having a value equal to approximately 2.0 volts is measured representing the intensity of the light which is transmitted through the outlet end 26 of the deposit pattern 30. Similarly, the remaining photodiode positions 2 through 2047 have associated therewith a voltage which is measured representing the intensity of the light which is received at that position.

Thus, the curve 60 shown in FIG. 4 represents a display of 2048 data points with each point representing the output of a respective photodiode 48. Such a display is generated by the computer 56 and is displayed on the information output display 58 using conventional data display techniques. As can be seen from FIG. 4, the 2048 data points combine to provide a substantially continuous profile of the intensity of the light received by the photodiodes 48 along the length of the deposit pattern 30. Because the intensity of the light received by each photodiode 48 in the exemplary embodiment is inversely related to the concentration of particles on the deposit pattern 30 at the photodiode position, the curve 60 also represents a substantially continuous profile, i.e., a "scan", of the particle concentration along the length of the deposit pattern 30.

Accordingly, the curve 60 in FIG. 4 describes a ferrogram 15 (FIG. 1) having a deposit pattern 30 with relatively low concentration of large sized particles at the inlet end 24 (position 1). Reading the curve 60 from left to right, the rise in the curve (designated 64) indicates a build up of particles near the inlet end 24. The relatively flat portion 66 of the curve 60 represents a relatively even size distribution of the particle concentration for medium and small sized particles (e.g., the range approximately between photodiode positions 400 to 1400). A local minimum 68 in the curve 60 represents a drop-off in the particle concentration for smaller sized particles of a size associated approximately with the photodiode position 1600. The fall in the curve (designated 70) represents the decline in particle concentration for very small particles at the outlet end 26 of the deposit pattern 30.

As is described more fully below, various trending mechanisms can be employed by the computer 56 to analyze automatically the profile data represented by the curve 60 and thus the ferrogram deposit pattern 30. For example, a conventional math software package installed on the computer 56 is utilized to integrate the area under the curve 60. As will be appreciated by those skilled in the art, the integration of the area under the curve 60 can be compared with previous ferrogram profile data obtained from the same machine or other "standard" profile data, for example, and can be used as a trending mechanism for the amount of wear generated by a machine component.

In addition, the computer 56 can utilize conventional math software to perform a trending analysis based on the calculated variance of the curve 60 around a spline curve reference. More particularly, the variance of the curve 60 around a spline curve reference will indicate a change in position of particles in different size ranges as will be appreciated. According to another trending mechanism, the computer 56 calculates the difference between the curve 60 and previously measured profile data stored in the computer 56 memory. The calculated difference is used to identify rapid changes in the build-up of wear particles and can be used to diagnose component wear in a machine. The results of each of the above types of trending analyses are output, for example, on the information output display 58.

Figure 5:
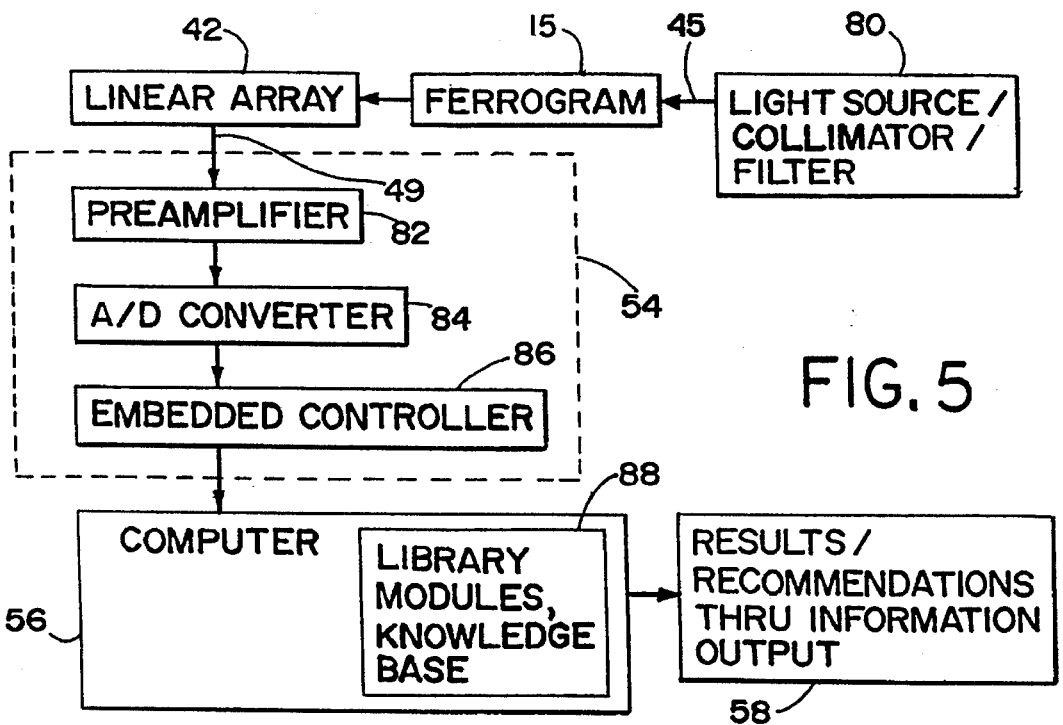
FIG. 5 is a detailed block diagram of the ferrogram scanning system of FIG. 2 in accordance with the present invention.

FIG. 5 represents a detailed block diagram of the ferrogram scanning system 35 of FIG. 2. The light source 43, fiber optic cables 44, light collimator 40 and filter 46 are shown collectively in block 80. Light 45 is transmitted through the ferrogram 15 and is received by the linear photodiode array 42. The photodiodes 48 in the array 42 provide their respective output signals serially to the signal processor 54 via line 49 as is described above. The signal processor 54 includes a preamplifier 82 for amplifying each output signal from the photodiodes 48. An analog-to-digital converter (ADC) 84 converts the analog output signals provided from the photodiodes 48 into digital signals for further analysis by the computer 56. An embedded controller 86 in the signal processor 54 provides the appropriate control, e.g., timing control, for reading the serial data from the photodiode array 42, amplifying the data, converting the data, and providing the data from the ADC 84 to the computer 56 according to conventional data processing techniques. As is explained more fully below with respect to FIGS. 8 and 9, the embedded controller 86 can also be used to control a holding mechanism for automatically positioning the ferrogram 15 between the light collimator 40 and the photodiode array 42.

The computer 56 receives the profile data from the signal processor 54 and stores the data in computer memory (not shown). Included in the computer memory is one or more library modules 88 which include, for example, historical scan data, component specific scan data, library and metallurgical scan data, and the like as is explained in more detail below in connection with FIG. 10. The computer 56 compares the profile data with the scan data in one or more of the library modules. These comparisons, such as variation about a spline curve, variation in the integral area beneath the curve, etc., are based on such comparisons, the computer 56 provides output data and/or recommendations regarding machine wear, maintenance, etc.

Figure 6:
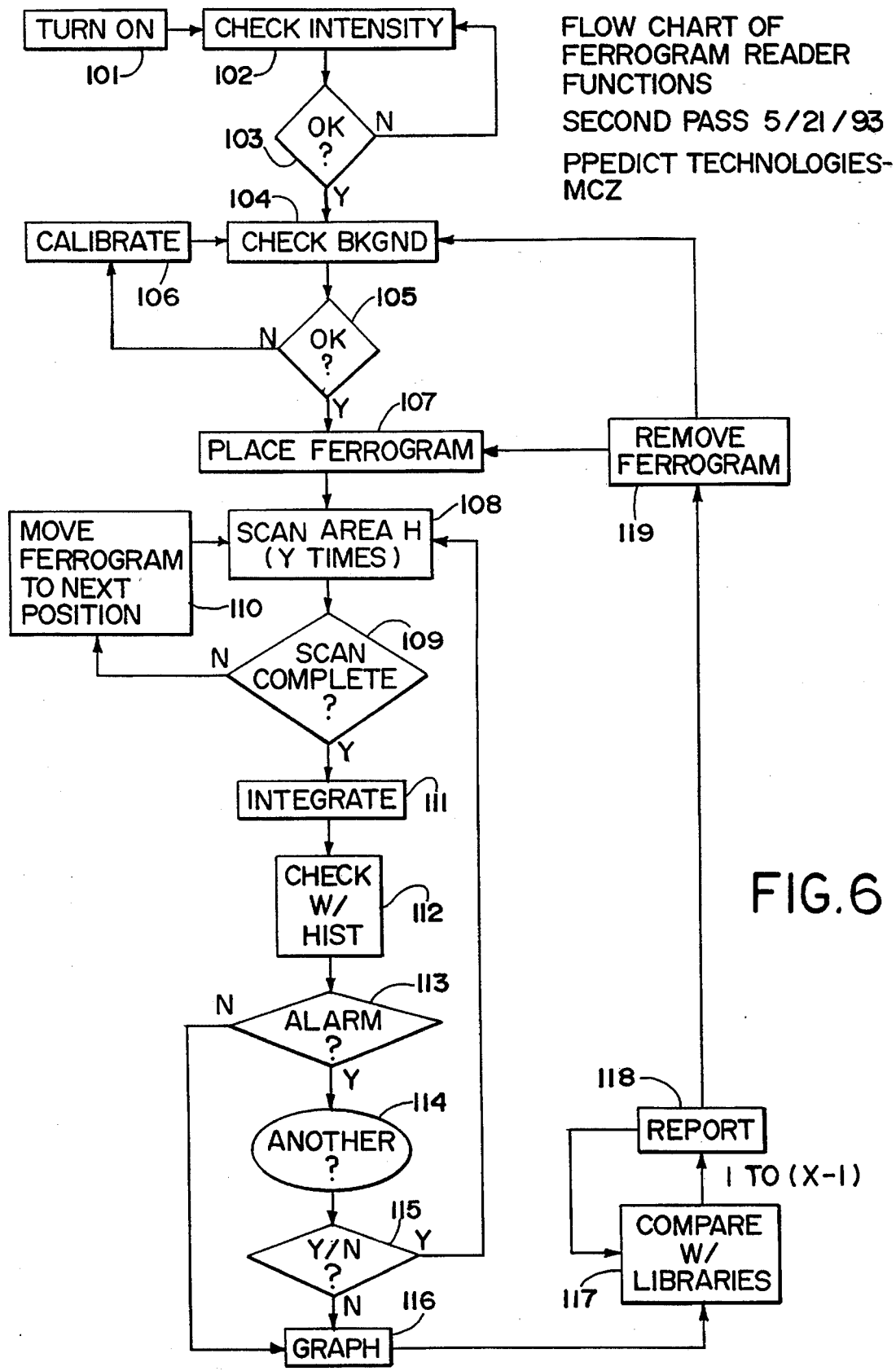
FIG. 6 is a system flowchart describing the operation of the system of FIG. 2.

Referring now to FIG. 6, a system flowchart describing the operation of the ferrogram scanning system 35 is shown. In step 101, the system 35 is powered up or otherwise turned on. With the ferrogram 15 not yet positioned between the light collimator 40 and the linear photodiode array 42, in steps 102 and 103 the system 35 checks the intensity level reading from each of the photodiodes 48 to determine whether the light source 43, light collimator 40 and linear photodiode array 42 are operating properly. If the intensity reading from each of the photodiodes 48 is not within an acceptable range, the system 35 continues to loop through steps 102 and 103 indicating a failure condition.

If in step 103 the intensity readings from each of the photodiodes are within an acceptable range, the system 35 proceeds to steps 104 and 105 whereby the background intensity level of the photodiode array 42 is evaluated. More specifically, the system 35 compares the output signal level from each photodiode 48 in the photodiode array 42 with the signal level of the other photodiodes 48 to determine whether there is an acceptable degree of uniformity. Non-uniformities may be caused, for example, due to contaminants on the photodiode array 42. To the extent the output signal levels of the photodiodes 48 are not uniform, the system 35 calibrates the output levels in step 106 by adjusting the gain provided to the respective photodiode(s) via the preamplifier 82 (FIG. 5). As a result, the output signals for each of the photodiodes 48 are normalized.

Following the initialization procedures of steps 101 through 106, the system 35 proceeds to step 107. In step 107, the system 35 prompts an operator via the information output display 58 to place the ferrogram 15 to be analyzed between the light collimator 40 and the photodiode array 42 using the holding brackets 37 (FIG. 2). The holding brackets 37 preferably are designed such that when the ferrogram 15 is initially placed in the holding brackets 37, the deposit pattern 30 is positioned with the light collimator 40 and photodiode array 42 in position A as is represented in FIG. 1. In step 108, the system 35 measures the output signals from each of the N photodiodes 48 and stores the data for the respective photodiode positions in memory in the computer 56. In the preferred embodiment, step 108 is repeated a predetermined Y number of times and the output signals for each photodiode position are averaged together and stored in memory. Such averaging reduces the effects of noise as will be appreciated.

Following step 108, the system 35 proceeds to step 109 in which it determines if the scan is complete, i.e., whether profile data has been obtained over the entire length of the deposit pattern 30. The system 35 may determine this automatically using an electro-optic sensor (not shown) for identifying the end of the deposit pattern 30. For example, the electro-optic sensor can be used to detect an end-of-pattern marker 109' (FIG. 1) on the ferrogram 15. Alternatively, the system 35 can prompt the operator to indicate (via a keypad or the like) whether the entire length of the deposit pattern 30 has been analyzed.

If the scan is not complete in step 109, the system 35 proceeds to step 110 in which the ferrogram 15 is moved relative to the light collimator 40 and photodiode array 42 to the next incremental position (e.g., position B as represented in FIG. 1). This is accomplished manually according to one embodiment whereby the system 35 prompts the operator to move the ferrogram 15 within the holding brackets 37 relative to the light collimator 40 and photodiode array 42 whereby the light collimator and photodiode array are in position B (FIG. 7). Alternatively, automatic positioning means such as a set of drive rollers controlled by the embedded controller 86 (see FIGS. 8 and 9) automatically move the ferrogram 15 relative to the light collimator 40 and photodiode array 42 to position B. Following step 110, the system 35 returns to step 108 where the output signals for the next N photodiode positions are measured, averaged and stored in memory in the computer 56. Steps 108–110 are repeated until the entire length of the deposit pattern 30 is scanned in increments of N photodiode positions to produce a substantially continuous profile of data points.

After the scan has been completed as determined in step 109, the system proceeds to step 111. In step 111, the computer 56 integrates the area under the profile data (e.g., curve 60). The value representing the integrated area under the profile data curve serves as a predetermined criteria upon which the ferrogram 15 under test can be evaluated. For example, in step 112 the computer 56 compares the value of the integrated area under the profile data curve with the integral values of previous profiles stored in the computer 56 memory. A change in the value of the integral as compared to previous profiles which exceeds a predetermined threshold value can be programmed in the computer 56 to indicate abnormal wear in the machine.

In step 113 the computer 56 determines whether the comparison in step 112 meets the predefined criteria. If not, the ferrogram scanning system 35 provides an audible and/or visual alarm to the operator via the information output 58 (FIG. 2). Such an alarm indicates an abnormal condition has been detected. In such case, the system 35 proceeds to step 114 whereby the computer 56 queries via the information output 58 whether the operator would like to repeat the scanning operation in case a measurement error may have occurred. The operator can respond via a keyboard input (not shown) on the computer 56. If the operator indicates that a repeat scan is desired in step 115, the system 35 returns to step 108 and the above-described scanning procedure is repeated. If the operator indicates in step 115 that a repeat scan is not desired, the system 35 proceeds to step 116 in which the profile data obtained from the photodiodes is displayed on the information output display 58 (e.g., as curve 60).

Referring again to step 113, if it is determined by the computer 56 that the comparison in step 112 does in fact meet the predefined criteria, an alarm is not sounded and/or displayed. Instead, the system 35 proceeds directly to step 116 and the profile data is displayed.

Following step 116, the system 35 in steps 117 and 118 performs one or more knowledge-based analyses on the profile data to aid in diagnosing wear conditions, incipient machine failure, and the like. More particularly, the computer 56 is programmed using conventional techniques to operate as an expert system in analyzing the profile data obtained from scanning the ferrogram deposit pattern 30. As is discussed in more detail below with respect to FIG. 10, in step 117 the computer 56 compares the profile data with one or more selected library modules stored in memory 88. The library modules are configured as part of an expert system knowledge base which enable the computer 56 to make decisions, recommendations, evaluations, etc. of machine conditions. The expert system preferably is rule based allowing for decisions, recommendations, evaluations, etc. to be made by the computer 56 by applying the appropriate rules to the scanned profile data. The rules for the expert system are created using known expert system techniques based on the experience and skill of those having expert skills in the field of ferrogram and wear particle analysis. As a result, the expert driven ferrogram scanning system 35 provides ferrogram analysis which is substantially independent of the knowledge and/or level of skill of the actual operator. Accordingly, the ferrogram scanning system 35 provides more accurate, consistent results. Such results are reported to the operator in step 118 via the information output 58.

The various expert analyses having been completed and reported in steps 117 and 118, the system 35 proceeds to step 119 in which the operator is prompted via the information output 58 to remove the ferrogram 15 from the holding brackets 37 and the system 35. Thereafter, the system 35 returns to step 104 where the system recalibrates itself in steps 104–106 in preparation for scanning another ferrogram 15.

Turning briefly to FIG. 7, the holding brackets 37 for holding the ferrogram 15 between the light collimator 40 and the photodiode array 42 are shown. The holding brackets 37 each include a notch 150 in which the edges of the ferrogram substrate 20 are slidably fitted to permit the ferrogram 15 to be slidably positioned in the direction of arrows 151 along the longitudinal axis A (FIG. 1). Thus, the ferrogram 15 can be positioned in increments of N photodiode positions (e.g., POS A and POS B in FIG. 1) in step 110 (FIG. 6) relative to the light collimator 40 and photodiode array 42. As a result, the entire length of the deposit pattern 30 is scanned.

FIG. 8 shows in relevant part an alternate embodiment of the ferrogram scanning system 35. Instead of holding brackets 37, a pair of rollers 37' are utilized to position the ferrogram 15 between the light collimator 40 and the photodiode array 42. At least one pair of rollers 37' is driven by a motor 156 controlled by the embedded controller 86 (FIG. 5). By controlling the rotation of the motor 156, the embedded controller 86 moves the ferrogram 15 automatically in step 110 (FIG. 6) N photodiode positions along the longitudinal axis A. The motor 156 can be a conventional stepper motor, for example. The amount which the ferrogram 15 is moved relative to the light collimator 40 and the photodiode array 42 is controlled based on the known degree of rotation of the motor 156 and the diameter of the rollers 37' as will be appreciated.

FIG. 8 shows in relevant portion another embodiment of the system 35. As in the embodiment of FIG. 7, rollers 37' and a motor 156 are provided for moving the ferrogram 15 along its longitudinal axis A. However, in the embodiment of FIG. 8 a single photodiode 48 is utilized in place of the photodiode array 42. The embedded controller 86 causes the motor 156 to move the ferrogram 15 at a constant rate along the direction of arrow 158. At the same time, the embedded controller 86 causes the output of the photodiode 42' to be sampled at a predefined rate by the signal processor 54. By controlling the rate of movement of the ferrogram 15 and the sampling rate, the system 35 obtains a series of data representing the intensity of the light transmitted through the ferrogram along the length of the deposit pattern 30. The series of data provides a substantially continuous profile data curve as will be appreciated. The computer 56 then analyzes the profile data in the same manner as is described above.

FIG. 10 illustrates graphically the various types of trending and other expert system based analyses which are performed by the ferrogram scanning system 35. The curve shown in block 200 represents the scanned profile data obtained in steps 108–110 of FIG. 6. The curve in block 202 represents historical scan data from an earlier ferrogram originating from the same machine presently being evaluated. Such machine can be, for example, a gearcase, compressor, etc. This historical scan data is stored in a library module in memory in the computer 56 and is compared with the current scan data as is described above with respect to step 112.

The curve in block 203 represents component specific scan data stored in a library module within the computer 56. The component specific scan data represents, for example, ferrogram information specific for a "normally wearing" machine having the same manufacturer, model, industry usage, etc. As an example of an expert analysis in step 117 of FIG. 6, the ferrogram profile data for a gearcase currently under test is compared by the computer 56 against a ferrogram profile data stored in the computer 56 memory representing a "normally wearing" gearcase. Based on such comparison, the computer 56 is programmed to apply an appropriate rule based analysis and to output data, conclusions and/or recommendations on the information output display 58. For example, the system 35 will recommend that the gearcase be serviced upon detecting abnormal wear.

Furthermore, the library modules 88 stored in the computer 56 can include "standard" scan data of known metallurgical and compositional content as represented by the curve in block 204. In step 117 (FIG. 6), the computer 56 compares the ferrogram scan data being evaluated with one or more of the standard library profiles to produce information about the composition of the particulate in the ferrogram 15. The system 35 in step 118 (FIG. 6) outputs such information along with any recommendations and conclusions.

The comparison of historical data and other library information with the current profile data and the relative weighting given to each comparison are incorporated by the system 35 into a knowledge based system that provides a recommendation of machine condition. The computer 56 can be programmed to perform the above described comparisons and/or operations using conventional programming techniques based on the disclosure provided herein by someone of ordinary skill in the art of programming. For example, commercially available programming languages having artificial intelligence capabilities such as PROLOG can be used to implement the desired knowledge based comparisons using conventional techniques.

It is noted that the terms "scan" data and "profile" data are used interchangeably herein and are intended to represent a substantially continuous set of data describing the particle concentration across the deposit pattern 30 with substantial resolution.

Although the invention has been shown and described with respect to certain preferred embodiments, it is obvious that equivalents and modifications will occur to others skilled in the art upon the reading and understanding of the specification. For example, the ferrogram scanning system 35 has been described herein as scanning the deposit pattern 30 in a transmissive mode whereby light is transmitted through the deposit pattern 30 and is subsequently detected. In another embodiment, the ferrogram scanning system 35 uses a reflective mode to scan the deposit pattern 30. The photo diode array 42 in such case would be configured to detect the intensity of light reflected from the deposit pattern 30 as will be appreciated.

Furthermore, although the ferrogram scanning system 35 has been described primarily in the context of processing the scan data digitally, it will be appreciated that the scan data can be processed and output in analog form as well. Also, although a photodiode array 42 is utilized in the exemplary embodiment to detect light, other devices such as a charge-coupled device, phototransistors, etc. can be utilized in place of the photodiode array. Even further, the exemplary embodiment utilizes visible light radiation to analyze the ferrogram. However, it will be appreciated that other embodiments may use different frequencies of radiation while remaining within the intended scope of the invention.

The present invention includes all such equivalents and modifications, and is limited only by the scope of the following claims.

What is claimed is:

1. An apparatus for analyzing particles collected from a fluid from a machine and deposited on a substrate along a given direction, said particles being arranged on said substrate along said given direction as a function of a respective size of said particles, said apparatus comprising:
   holding means for supporting said substrate;
   radiation source means for directing radiation toward the particles on said substrate;
   radiation detector means for receiving radiation incident upon the particles on said substrate and for providing an output based on a concentration of said particles, said radiation detector means being cooperative with said radiation source means to output substantially continuous profile data indicative of the concentration and size distribution of said particles along said given direction, said substantially continuous profile data being continuous with respect to spatial location alone said given direction; and
   automated means for processing said substantially continuous profile data to ascertain a characteristic of said machine.

2. The apparatus of claim 1, wherein said radiation source means comprises a light source.

3. The apparatus of claim 1, wherein said radiation detector means comprises a photodiode array.

4. The apparatus of claim 3, wherein said photodiode array provides an optical resolution of at least about one thousand twenty-four data points per inch.

5. The apparatus of claim 1, wherein said particles comprise wear particles.

6. The apparatus of claim 1, further comprising output means for providing a display of said profile data.

7. The apparatus of claim 1, said automated means comprising computer means for comparing said profile data with reference data according to a predefined criteria, and output means for outputting information as a function of said comparison.

8. The apparatus of claim 7, wherein said particles comprise wear particles, and said output information relates to a condition of said machine.

9. The apparatus of claim 7, wherein said computer means is an expert system.

10. The apparatus of claim 1, wherein said automated means comprises means for evaluating a curve formed by said substantially continuous profile data.

11. An apparatus for analyzing wear particles collected from a fluid from a machine and deposited on a substrate along a given direction, said particles being arranged on said substrate along said given direction as a function of a respective size of said particles, said apparatus comprising:
    holding means for supporting said substrate;
    radiation source means for directing radiation toward the particles on said substrate;
    radiation detector means for receiving radiation incident upon the particles on said substrate and for providing an output based on a concentration of said particles, said radiation detector means being cooperative with said radiation source means to output substantially continuous profile data indicative of the concentration of said particles along said given direction, said substantially continuous profile data being continuous with respect to spatial location along said given direction; and
    computer means configured as an expert system including a knowledge base for analyzing said substantially continuous profile data and providing information relating to a condition of said machine.

12. The apparatus of claim 11, wherein said knowledge base includes historical data relating to said machine.

13. The apparatus of claim 11, wherein said knowledge base includes information specific to a type of said machine.

14. The apparatus of claim 11, wherein said knowledge base includes information relating to at least one of metallurgical or compositional content.

15. The apparatus of claim 11, wherein said radiation source means comprises a light source.

16. The apparatus of claim 11, wherein said radiation detector means comprises a photodiode array.

17. The apparatus of claim 11, further comprising output means for providing a display of said output data.

18. The apparatus of claim 11, wherein said computer means comprises means for evaluating a curve formed by said substantially continuous profile data.

19. A method for analyzing particles collected from a fluid from a machine and deposited on a substrate along a given direction, said particles being arranged on said substrate along said given direction as a function of a respective size of said particles, said method comprising the steps of:
    irradiating the particles on said substrate with a source of radiation;
    receiving radiation incident upon the particles on said substrate and providing an output signal based on a concentration of said particles;
    combining said irradiating and receiving steps whereby said output signal provides substantially continuous profile data indicative of the concentration of said particles along said given direction, said substantially continuous profile data being continuous with respect to spatial location along said given direction; and processing said substantially continuous profile data to ascertain a characteristic of said machine.

20. The method of claim 19, the step of analyzing said profile data comprising using a computer configured as an expert system.

21. The method of claim 20, wherein said expert system includes a knowledge base comprising historical data relating to said machine.

22. The method of claim 20, wherein said expert system includes a knowledge base comprising data specific to a particular type of said machine.

23. The method of claim 19, wherein said radiation comprises light.

24. The method of claim 19, said processing step comprising evaluating a curve formed by said substantially continuous profile data.

* * * * *